United States Patent [19]
Stoop et al.

[11] Patent Number: 5,767,791
[45] Date of Patent: Jun. 16, 1998

[54] LOW-POWER CIRCUIT AND METHOD FOR PROVIDING RAPID FREQUENCY LOCK IN A WIRELESS COMMUNICATIONS DEVICE

[75] Inventors: Michael D. Stoop, Aliso Viejo; Terry E. Flach, Altadena, both of Calif.

[73] Assignee: Vitalcom, Tustin, Calif.

[21] Appl. No.: 677,095

[22] Filed: Jul. 9, 1996

Related U.S. Application Data

[60] Provisional application No. 60/006,600, Nov. 13, 1995.

[51] Int. Cl.$^6$ ............................ G08C 19/04; G08C 19/10
[52] U.S. Cl. ........................ 340/870.11; 340/286.07; 340/825.72; 455/375; 455/119; 455/343; 128/903
[58] Field of Search ................................. 455/75, 76, 77, 455/34.3, 119, 120, 125; 340/870.11, 286.06, 286.07, 573, 825.19, 825.72; 128/630, 903

[56] References Cited

U.S. PATENT DOCUMENTS

| | | | |
|---|---|---|---|
| 3,925,762 | 12/1975 | Heitlinger et al. | 340/150 |
| 4,051,522 | 9/1977 | Healy et al. | 358/86 |
| 4,521,918 | 6/1985 | Challen | 455/75 |
| 4,531,526 | 7/1985 | Genest | 128/903 |
| 4,573,026 | 2/1986 | Curtis et al. | 455/75 |
| 4,955,075 | 9/1990 | Anderson | 455/343 |
| 4,958,645 | 9/1990 | Cadell et al. | 128/903 |
| 5,205,294 | 4/1993 | Flach et al. | 128/696 |
| 5,238,001 | 8/1993 | Gallant et al. | 128/700 |
| 5,270,811 | 12/1993 | Ishibashi et al. | 358/108 |
| 5,305,202 | 4/1994 | Gallant et al. | 364/413.06 |
| 5,305,353 | 4/1994 | Weerackody | 375/100 |
| 5,309,920 | 5/1994 | Gallant et al. | 128/710 |
| 5,359,641 | 10/1994 | Schull et al. | 379/106 |
| 5,375,604 | 12/1994 | Kelly et al. | 128/671 |
| 5,377,222 | 12/1994 | Sanderford, Jr. | 375/1 |
| 5,381,798 | 1/1995 | Burrows | 128/696 |
| 5,416,695 | 5/1995 | Stutman et al. | 364/413.02 |
| 5,438,329 | 8/1995 | Gastouniotis et al. | 340/870.02 |
| 5,441,047 | 8/1995 | David et al. | 128/670 |
| 5,458,122 | 10/1995 | Hethuin | 128/696 |
| 5,458,123 | 10/1995 | Unger | 128/696 |
| 5,507,035 | 4/1996 | Bantz et al. | 455/133 |
| 5,579,001 | 11/1996 | Dempsey et al. | 340/870.01 |
| 5,579,378 | 11/1996 | Arlinghaus, Jr. | 379/106 |
| 5,646,701 | 7/1997 | Duckworth et al. | 340/825.72 |

FOREIGN PATENT DOCUMENTS

| | | |
|---|---|---|
| 2258960 | 2/1993 | United Kingdom. |
| 2271691 | 4/1994 | United Kingdom. |

OTHER PUBLICATIONS

PCT International Search Report, dated Jan. 22, 1997, for Internationl Application PCT/US96/15233.
PCT Written Opinion, dated Aug. 11, 1997, for International Application PCT/US96/15233.
Product brochure titled "Wireless Connectivity by Pacific Communications, Inc.", 1993.

*Primary Examiner*—Jeffrey Hofsass
*Assistant Examiner*—Timothy Edwards, Jr.
*Attorney, Agent, or Firm*—Knobbe, Martens, Olson & Bear, LLP

[57] ABSTRACT

A two-way medical telemetry system is provided for displaying and monitoring, at a central location, physiologic and other patient data of multiple, remotely-located patients. The system comprises multiple battery-powered remote telemeters, each of which is worn by a respective patient, and a central station which receives, displays and monitors the patient data received (via RF) from the remote telemeters. The telemeters communicate with the central station using a two-way TDMA protocol which permits the time sharing of timeslots, and which uses a contention slot to permit telemeters to transmit service requests to the central station. Two-way spacial diversity is provided using only one antenna and one transceiver on each remote telemeter. The remote telemeters include circuitry for turning off the active transceiver components thereof when not in use (to conserve battery power), and include circuitry for performing a rapid, low-power frequency lock cycle upon power-up. The system has multiple modes of operation, including a frequency hopping (spread spectrum) mode and a fixed frequency mode, both of which preferably make use of the 902–928 MHz ISM band. Patient locators are provided to allow the clinician to track the location of each patient.

27 Claims, 7 Drawing Sheets

LOW-POWER CIRCUIT AND METHOD FOR PROVIDING RAPID FREQUENCY LOCK IN A WIRELESS COMMUNICATIONS DEVICE

PRIORITY CLAIM

This application claims the benefit of U.S. Provisional Application No. 60/006,600 titled TWO-WAY TDMA TELEMETRY SYSTEM, filed Nov. 13, 1995.

FIELD OF THE INVENTION

The present invention relates to wireless communications systems of the type which employ portable, battery-powered communication devices. More particularly, the present invention relates to a circuit and method for providing rapid frequency lock in an ambulatory medical telemetry device or other battery-powered TDMA device.

BACKGROUND OF THE INVENTION

Medical telemetry systems that allow the physiologic data of multiple, remotely-located patients to be monitored from a central location are known in the art. These systems typically comprise remote RF transmitters that plug into conventional bedside monitors. Each remote transmitter receives physiologic data from the corresponding bedside monitor, and transmits this data via an RF telemetry link to a central monitoring station. This physiologic data is generated by sensors that are connected to the patient, and may include, for example, electrocardiograph (ECG) waveforms, $CO_2$ levels, and temperature readings. The sensing circuitry and remote RF transmitter (or transceiver, in the case of a two-way system) are referred to collectively herein as the "remote telemeter," or simply "telemeter."

With a telemetry system, the physiologic data of a patient can be viewed by the clinician at either the patient's bedside monitor or at the central station. Because these systems use telemetry to transfer the physiologic data, as opposed to cables running between the bedside monitors and the central station, the systems can rapidly and inexpensively be installed within a hospital or clinic.

A significant problem that has been encountered in the art of medical telemetry relates to the frequency and, more importantly, the power at which the telemetry devices can transmit their RF signals. Until the enactment by the Federal Communications Commission (FCC) of Part 15.247 of the FCC Rules and Regulations, medical telemetry systems were primarily limited to the VHF band (174–216 MHz), and could only operate at very low transmission powers of less than 0.1 milliwatts (mW). (See FCC Part 15.241.) This restriction on the transmission power has significantly limited the transmission range (i.e., the maximum distance between the transmitter and the receiver) of the telemetry devices. Restrictions also place limits on the data rate or "bandwidth" at which the telemetry devices can transmit data.

With the enactment of Part 15.247 in 1985, the FCC authorized the use of the 902–928 MHz Industrial, Scientific, and Medical (ISM) band. Under Part 15.247, telemetry systems can transmit at a power of up to one Watt within the ISM band, provided that the systems use either a direct sequencing or a frequency hopping spread spectrum modulation technique, as set forth in Part 15.247. (Spread spectrum is a well known modulation technique in which the signal is spread over a wide range of frequencies.) In order to take advantage of this higher power transmission, some companies have developed bedside spread spectrum telemetry systems that operate in the ISM band. At least some of these systems are two-way systems, in which data can be transferred in both directions (i.e., from the remote telemeter to the central station, and vice versa).

Although it is now possible to achieve greater transmission ranges by using an approved spread spectrum technique within the ISM band, ISM band systems tend to be more susceptible to multi-path interference than VHF systems. Multi-path interference occurs when a signal takes two or more paths (as the result of signal reflections) from the transmitter to the receiver such that the multi-path components interfere with each other. When the multi-path components are out of phase with one another at the receiver's antenna, the components cancel one another, causing the receive signal to drop out or "fade." This phenomenon is know as Rayleigh fading. One solution to Rayleigh fading has been to provide two separate receiver/antenna pairs on each remote telemeter of the spread spectrum system (and on the central station), with the antennas spaced apart from another by a predetermined distance. With this technique, known as spacial diversity, when one of the antennas experiences multi-path fading, the other antenna (and the corresponding receiver) is used to receive the signal. One problem with this method is that it adds to the cost, size and complexity of the remote transceiver.

Although bedside medical telemetry systems have been developed which take advantage of the ISM band, the medical telemetry industry has been generally unsuccessful at producing an ambulatory medical telemetry system of this type. (In an ambulatory system, the remote telemeters are portable, battery-powered devices that are worn by the patients. Because no connection to either a power outlet or bedside monitor is needed, the patient is mobile while being monitored.) The power inefficiency of existing remote transceiver designs is a principal cause of the inability to produce an ambulatory system which takes advantage of the ISM band; this inefficiency has prevented obtaining a suitable battery life while operating at the higher powers permitted under Part 15.247.

In addition to authorizing the use of the ISM band under Part 15.247, the FCC also permits medical telemetry systems to use the ISM band under Part 15.249. Part 15.249 allows non-spread spectrum operation in the ISM band, but only at a transmission power of about 750 microwatts (µW). Although operating in the ISM band without using either direct sequencing or frequency hopping carries a number of benefits (such as the ability to operate a greater number of telemetry systems in close proximity to one another), the power restriction to 750 µW has apparently deterred the medical telemetry industry from taking advantage of this mode of operation. A need thus exists in the art for a telemetry system which flexibly makes use of the various possible modes of operation permitted within the ISM band, and which takes advantage of the potential benefits that exist for each such mode. A need also exists in the art for a medical telemetry system that can flexibly be upgraded to take advantage of new frequency bands as such bands are released by the FCC.

SUMMARY OF THE INVENTION

One object of the invention is to provide a medical telemetry system in which the remote transceivers conserve battery power to the greatest extent possible. Another object is to provide an ambulatory system in which the remote transceivers can transmit at a relatively high power (e.g., 25 mW or higher) while maintaining a reasonable battery life when using, for example, a 9-volt or AA-size alkaline or lithium battery. An additional object is to provide a low-power method of rapidly locking the carrier frequency of a battery-powered telemeter upon power-up of the telemeter's transmitter components.

In accordance with these and other objects of the invention, there is provided a two-way medical telemetry system for displaying and monitoring, at a central location, physiologic and other patient data of multiple, remotely-located patients. In the preferred embodiment, the system comprises multiple battery-powered remote telemeters, each of which is worn by a respective patient, and a central station which receives, displays and monitors the patient data received (via RF) from the remote telemeters. In the preferred embodiment, the remote telemeters communicate with the central station using a two-way TDMA protocol in which individual telemeters are uniquely assigned timeslots during which to transmit their respective telemetry packets (containing real-time patient data) to the central station, and in which the central station broadcasts control packets (containing timeslot assignments and other control information) to the telemeters during separate control timeslots. The system has multiple modes of operation, including a frequency hopping (spread spectrum) mode and a fixed frequency mode, both of which preferably make use of the 902–928 MHz ISM band. Two-way spacial diversity is provided using only one antenna and one transceiver on each remote telemeter.

In accordance with the invention, each battery-powered telemeter includes power-conservation hardware and firmware for maintaining various components of the respective telemeter's transceiver in a low-power state during TDMA timeslots for which the telemeter is neither transmitting nor receiving data. For example, each telemeter is configured to maintain its amplifier, programmable phase-lock loop chip and voltage-controlled oscillator in respective low power states during timeslots for which other telemeters are transmitting, and to wake-up these components just prior to the transmission timeslot to which the telemeter is assigned. The provision of such power-conservation hardware and firmware allows the battery-powered telemeters to operate for extended periods of time, at the higher transmission powers permitted within the ISM band, using standard 9-volt or AA-size alkaline or lithium batteries.

In accordance with another aspect of the invention, each telemeter includes hardware and firmware for rapidly locking the carrier frequency of the telemeter's transceiver upon power-up of the transceiver components. In the preferred embodiment, the hardware includes a programmable phase-lock loop (PLL) chip coupled to a voltage controlled oscillator (VCO) to form a standard phase-lock loop (PLL) circuit. In addition, a sample-and-hold (S/H) circuit is connected between the PLL chip and the VCO such that the loop of the PLL circuit is open when the S/H circuit is in a HOLD state, and is closed when the S/H circuit is in the SAMPLE state. The firmware includes associated code (which runs on a microprocessor of the telemeter) for performing a fast-frequency lock operation just before the telemeter's transmit time.

In operation, the firmware program initiates a phase-lock process by powering up the VCO and PLL chip and initiating a phase-lock process. Once the carrier frequency (at the output of the VCO) settles to within a selected acceptable margin of frequency error, but before the PLL circuit has reached a state of phase-lock, the program opens the sample-and-hold circuit to interrupt the phase-lock process, to thereby hold the carrier frequency at a steady value. (In the preferred embodiment, this is accomplished by waiting a predetermined delay before opening the S/H circuit; to ensure that this delay corresponds to the acceptable margin of frequency error, a programmable gain constant of each telemeter's programmable PLL chip is adjusted during telemeter calibration.) This allows the telemeter to begin transmitting its data, without having to wait for the phase-lock process to complete. The selected margin of frequency error is selected such that the central station accurately receives the data transmissions from the remote telemeters (without special receiver circuitry) as though transmitted using the correct carrier frequency. To further conserve battery power, the PLL chip is placed in a low-power state as soon as the carrier frequency is locked, and is maintained in the low-power state as the telemeter transmits its data.

This ability to rapidly lock the carrier frequency upon transceiver power-up significantly reduces the dead time (i.e., the time during which no meaningful data is transmitted) between successive transmissions of different telemeters. (Because the process of locking the carrier frequency generally creates considerable noise, it is undesirable to overlap the transmission of one telemeter with the frequency lock of the next telemeter.) Thus, in addition to conserving battery power, the fast frequency lock circuitry and process provide for a greater utilization of RF bandwidth.

BRIEF DESCRIPTION OF THE DRAWINGS

These and other objects and features of the invention are described below with reference to the drawings of a preferred embodiment, which is intended to illustrate and not to limit the invention.

In the drawings, the first digit of each reference number indicates the figure in which the item first appears.

DETAILED DESCRIPTION OF THE PREFERRED EMBODIMENTS

For convenience, the description of the preferred embodiment is arranged under the following seven major headings: SYSTEM OVERVIEW; TDMA OPERATION AND DIVERSITY; ALLOCATION OF BANDWIDTH TO TELEMETERS; OPERATIONAL MODES; REMOTE TRANSCEIVER CIRCUITRY; REMOTE TRANSCEIVER OPERATION; and CENTRAL TRANSCEIVER.

1. System Overview

Figure 1:
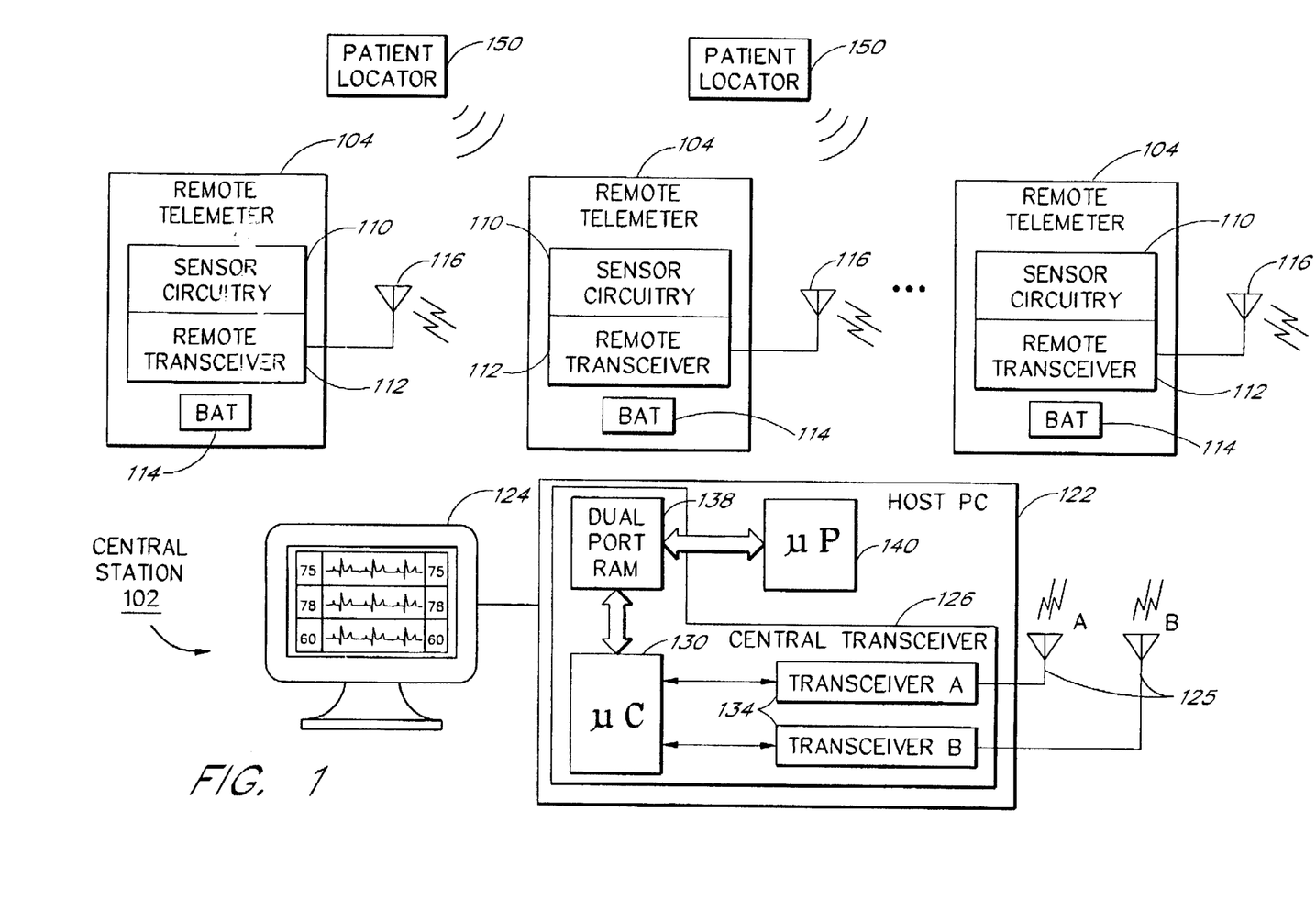
FIGS. 1 and 2 illustrate the primary components of a medical telemetry system in accordance with the present invention, with FIG. 2 illustrating how the remote, battery-powered telemeter of FIG. 1 may be worn by an ambulatory patient.
Figure 2:
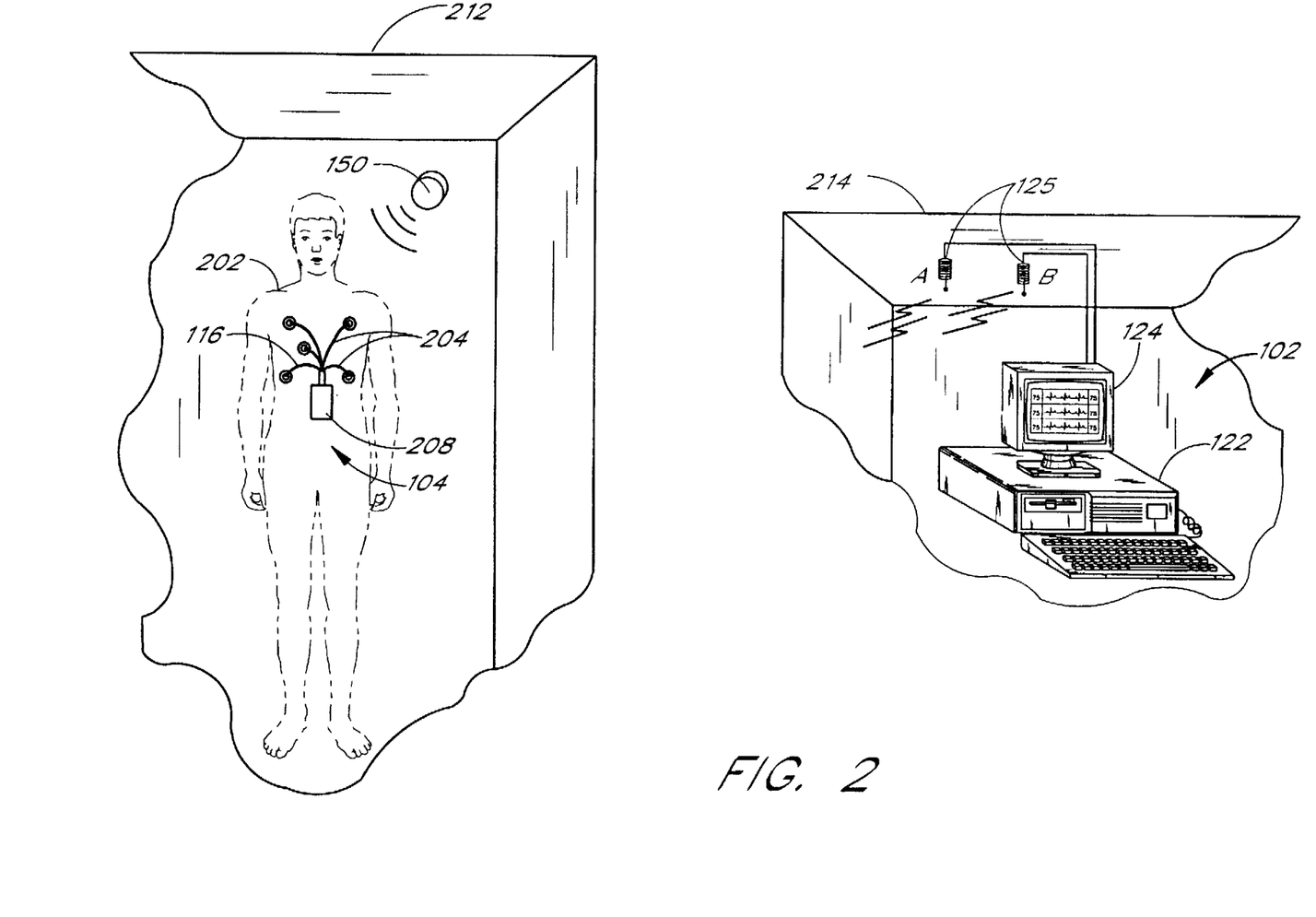

FIGS. 1 and 2 illustrate a two-way medical telemetry system in accordance with the present invention. The system includes a central monitoring and control station 102 ("central station") which communicates via radio frequency ("RF") with a plurality of battery-powered, portable, remote telemeters 104. The system also includes a plurality of battery-powered patient locator devices ("patient locators") 150, which transmit location signals to the remote telemeters 104.

Each remote telemeter 104 connects to and senses the physiologic data of a respective patient 202. This physiologic data may include, for example, waveform data such as ECG signals (sensed by ECG electrodes 204 connected to the patient), and may include numeric data such as blood pressure, $CO_2$, and temperature readings. The telemeters 104 may additionally sense and/or generate various types of non-physiologic data, such as patient voice signals produced by portable patient microphones, battery-level status data, ECG loose-lead status data, and patient location data. The physiologic and non-physiologic data sensed and/or generated by the remote telemeters 104 will be collectively referred to herein as "patient data."

The patient data sensed by the telemeters 104 is transmitted to the central station 102. As illustrated in FIG. 2, the central station 102 and the patient 202 may be located in different rooms 212, 214 or areas of the clinic. The central station 102 displays (or in the case of voice, outputs to a speaker) the patient data it receives, and monitors the patient data for predefined conditions (such as abnormally high temperature readings). The central station 102 also transmits various control data to the telemeters 104 of the system. To provide a greater coverage area and patient monitoring capacity, multiple "central stations" can be strategically positioned throughout the hospital, with the central stations interconnected by a wired local area network (LAN) so that the physiologic data of all patients can be monitored from one or more monitoring stations of the LAN.

The data transmissions of the central station 102 and of the respective telemeters 104 are separated in-time from one another using a time-division multiple-access (TDMA) scheme in which each transmitting device is assigned a unique timeslot during which time to transmit its data. (As described below, certain types of requests are alternatively transferred using a contention protocol.) In contrast to frequency division multiplexing systems, in which at least one receiver must be provided at the central station for each remote telemeter (since each telemeter operates on its own unique frequency), the TDMA system of the preferred embodiment communicates with all remote telemeters 104 of the system (which can be as high in number as 320 in the preferred embodiment) using only two transceiver/antenna pairs at the central station 102. All data transfers between central station 102 and the telemeters 104 are performed using a conventional frequency-shift keying (FSK) modulation technique.

With reference to FIG. 1, each telemeter 104 includes sensor circuitry 110, a single microcontroller-based remote transceiver 112, a battery 114, and a single antenna 116. The sensor circuitry 110 included within a given telemeter 104 depends upon the type or types of patient data sensed by the telemeter. For example, the sensor circuitry 110 of a telemeter 104 that senses and transmits multi-channel ECG waveform data will be configured to receive, digitize and multiplex ECG signals produced by corresponding ECG leads 204 (FIG. 2). The data sensed via the sensor circuitry 110 is provided to the remote transceiver 112 for transmission to the central station 102. The battery 114 is preferably a 9-volt or AA-size alkaline or lithium battery.

With further reference to FIGS. 1 and 2, the sensor circuitry 110, remote transceiver 112 and battery 114 of each respective telemeter 104 are preferably fully contained within a compact housing 208, and the telemeter 104 is worn by the patient 202, with one of the leads serving as the antenna 116. As a result of the wireless, light-weight design of the remote telemeter 104, the patient 202 can be ambulatory while being monitored. In another embodiment, the remote transceiver 112 and antenna 116 are packaged as a separate device that can be connected to a variety of portable bedside monitors (not shown), such as a Dynamap available from Johnson and Johnson Medical Instruments, and the remote transceiver is powered by the battery of the portable bedside monitor.

Each remote transceiver 112 advantageously includes special hardware and firmware for maintaining the active components of the transceiver in a low-power state when these components are not in use. This enables the remote telemeter 104 to be powered by the battery 114 for extended periods of time (typically 24 hours), allowing for a high degree of patient mobility. The remote transceiver 112 also includes hardware and firmware for enabling the telemeter 104 to be switched (either by the clinician or automatically via software) between various modes of operation, including a frequency-hopping (spread spectrum) mode which complies with Part 15.247 and a fixed-frequency mode which complies with Part 15.249. The power conservation and mode-switching features of the remote transceivers are described in detail below.

In the preferred embodiment, the central station 102 includes a host personal computer (PC) 122 (such as a Pentium class PC), a high resolution monitor 124, and a pair of antennas 125 (labelled "A" and "B" in FIGS. 1 and 2). The PC 122 executes medical monitoring software which is typically adapted to the specific needs or applications of the clinic in which the system is installed. For example, the monitoring software may be configured to monitor cardiac rehabilitation patients during stress testing, or may be configured to monitor the patients in the general care areas of a hospital. The monitoring software includes communications routines for communicating with the remote telemeters 104.

The PC 122 includes a central transceiver 126 which is preferably in the form of an add-on card that inserts into an I/O slot of the PC's motherboard. Preferably, the central transceiver 126 includes 2 kilobytes of dual-port dynamic random access memory ("dual-port RAM") 138, and includes a pair of redundant, microcontroller-based transceivers 134, which are respectively labeled in FIG. 1 as "transceiver A" and "transceiver B." The transceivers 134 preferably use conventional direct digital synthesis (DDS) for frequency control. Direct digital synthesis has the advantage of allowing the transmit and receive frequencies to be changed rapidly (typically within a few µs), as is desirable for frequency hopping operation. (Because DDS requires a relatively high amount of current, it is preferably not used in the battery-powered telemeters 104.)

The transceivers 134 are controlled by a microcontroller (µc) 130, which is a 17C42 available from Microchip, Inc. in the preferred embodiment. The microcontroller 130 interfaces with the dual-port RAM 138. The dual-port RAM 138 is used to transfer data between the microprocessor (µp) 140 of the host PC and the microcontroller 130 of the central transceiver 126.

Transceivers A and B are connected, respectively, to antennas A and B. Antennas A and B are appropriately spaced apart from one another to provide effective spacial diversity. (This is because Rayleigh fading or "drop out" due to multi-path interference can be reduced significantly by spacing two redundant antennas at least a quarter wavelength away from each other, and by dynamically selecting the antenna which receives the strongest signal.) As set forth below, the spacial diversity achieved via antennas A and B is "two-way" spacial diversity, meaning that its benefit is realized on transmissions in both directions.

All data transfers between the central station 102 and the telemeters 104 are in the form of packets, with each packet emanating from a single transmitting device. Each packet preferably includes an 8-bit error detection code, which is calculated using a conventional cyclic redundancy check (CRC) algorithm. In other embodiments, error correction codes may be used. Because of the high degree of reliability achieved through the combined use both spacial diversity and time diversity (discussed below), there is no need for an acknowledgement scheme. As will be recognized, however, the software and firmware of the system could easily be modified to make use of acknowledgment packets.

The microcontroller 130 of the central transceiver 126 runs a firmware program which moves packet data between the redundant transceivers 134 and the dual-port RAM 138 according to a particular TDMA timing protocol (described below). Packets received by transceivers A and B are written by the microcontroller 130 to the dual-port RAM 138, without initially being checked for errors. These packets are then read by the host PC's microprocessor 140 (under the control of the PC software), which performs error checking on the received data. Control packets to be sent by the central station 102 to the telemeters 104 are written to the dual-port RAM 138 by the microprocessor 140, and are then read by the microcontroller 130 and passed to the transceivers 134. The dual-port RAM 138 is divided into two sections, allowing one section of RAM to be filled with incoming patient data and service requests from the telemeters 104 while the other section is being read by the host PC's microprocessor 140.

With further reference to FIGS. 1 and 2, the system preferably includes a plurality of batter-powered patient locators 150. The patient locators 150 are small, low-power transmitters which may be strategically positioned throughout the clinic area to permit the tracking of the respective locations of the patients being monitored. Patient locators 150 may be attached, for example, to the walls or ceilings of various patient rooms, patient bathrooms, and diagnostic areas of a hospital, as generally illustrated in FIG. 2.

Each patient locator 150 is assigned a unique digital code, referred to herein as the "location code." In operation, each patient locator 150 remains in a periodic 16-second cycle in which it continuously transmits its location code (at a power of approximately ten microwatts) for a period of one second, and then shuts off (i.e., stops transmitting) for a period of 15 seconds. (In other embodiments, each patient locator 150 may be implemented as a transponder that transmits its location code only in response to a query from a remote telemeter 104.) The patient locators 150 transmit their respective location codes on the same RF frequency, which is preferably different from the transmit frequency (or frequencies) used by the central station 102 and the telemeters 104. When a patient moves sufficiently close to a patient locator 150 (e.g., within 5–10 feet), the patient's telemeter 104 receives the patient locator's unique location code, and relays this code to the central station with the patient data. The central station 102 then maps this code to the corresponding physical location, allowing the clinician to (selectively) view the location of the patient on the monitor 124. In the preferred embodiment, the location codes include a field for indicating whether the battery of a patient locator 150 is low.

2. TDMA Operation and Diversity

Figure 3:
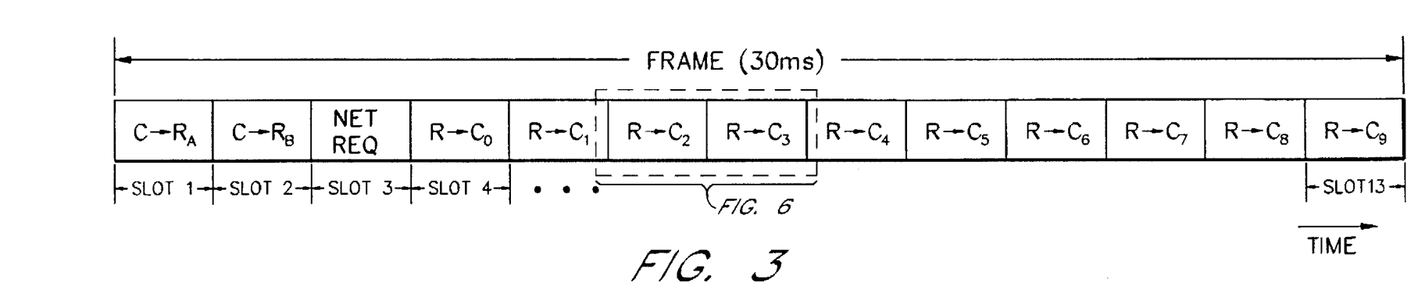
FIG. 3 illustrates a preferred TDMA sequence for transferring data between the central station and remote telemeters in accordance with the present invention.

FIG. 3 illustrates the preferred TDMA method used for transferring data packets between the central station 102 and the telemeters 104. Each 30 ms frame includes 13 timeslots. With the exception the timeslot labeled "NET REQ" in FIG. 2, each timeslot is uniquely allocated to a single transmitting device. The timeslots labeled "C→R" in FIG. 3 are used for transfers of synchronization and control information from the central station to the remote telemeters 104, with the subscripts "A" and "B" indicating the antenna/transceiver pair used for the transmission. The timeslots labeled "R→C" in FIG. 3 are used for transfers of patient data from individual telemeters 104 to the central station 102, with the subscripts 0–9 indicating the R→C timeslot number.

The timeslot labeled NET REQ is a special network request timeslot, which may be used by the telemeters 104 to send service requests to the central station 102. Unlike the C→R and R→C timeslots, the network request timeslot is a "contention" slot which is not assigned to any particular device. During the network request timeslot, any telemeter 104 can attempt to send its respective service request to the central station 102. If a collision occurs (when two or more telemeters transmit simultaneously), a conventional back-off algorithm (such as the binary exponential back-off algorithm used in Ethernet networks) is used by the transmitting devices to determine when to reattempt their respective network request transmissions. Because service requests are transmitted by the telemeters relatively infrequently, this use of a shared, contention timeslot (as opposed to having telemeter-specific network request timeslots) provides for a high degree of bandwidth efficiency.

The general TDMA operation of the system will now be described. During the first timeslot (labeled C→$R_A$ in FIG. 3) of each 30 ms frame, the central station 102 transmits a control packet on antenna A. During the following timeslot, the central station 102 re-transmits the same control packet on antenna B. During the C→$R_A$ timeslot, each telemeter 104 receives the control packet and checks the error detection code contained therein. If no errors are detected by a given telemeter 104, that telemeter does not attempt to receive the retransmitted packet on the following (C→$R_B$) timeslot. If, however, the telemeter 104 detects an error in the C→$R_A$ control packet, the telemeter discards the packet and receives the redundant packet transmitted during the C→$R_B$ timeslot. Because each control packet is transmitted from a different one of the antennas, the likelihood of data loss due to multi-path interference is significantly reduced. The likelihood that a telemeter 104 will miss the control packet due to interference is further reduced by the time diversity (i.e., the separation in time between the redundant transmissions) provided by this transmission scheme. Although the C→$R_A$ and C→$R_B$ control packets are transmitted on the same frequency in the preferred embodiment, these control packets can alternatively be transmitted on different frequencies to provide frequency diversity.

As will be appreciated by those skilled in the art, the above-described system and method for sending data from the central station to the telemeters 104 provides significant cost, size and power savings over prior art spacial diversity designs: As described above, in order to achieve spacial diversity on C→R transmissions, prior art systems have included redundant antennas and receivers on each telemeter. The present system, in contrast, eliminates the need for multiple receivers/antennas on the telemeters 104 without loosing the benefit of spacial diversity. (As set forth above, this is accomplished by transmitting each control packet twice, once from each of the two separate locations, so that the same receiver can be used to capture the redundant transmissions.) In addition to reducing the cost of the telemeter 104, the elimination of the redundant antenna and receiver in the telemeter results in a smaller telemeter device which uses less power—characteristics that are particularly advantageous in ambulatory and other battery-powered applications.

With further reference to FIG. 3, the ten consecutive timeslots labeled R→$C_0$–R→$C_9$ are allocated by the central station 102 to the individual telemeters 104 for the transmission of patient data. During each R→C timeslot, a single telemeter 104 transmits a packet. The central transceiver 126 receives this packet via both antenna/transceiver A and antenna/transceiver B, simultaneously capturing two versions of the same packet (referred to herein as the "A version" and the "B version").

Both versions of the received control packet are written by the microcontroller 130 to the dual-port RAM 138. The host PC 122 then proceeds to check the error detection code in the A version of the packet. If no errors are detected, the A version is kept and the B version is discarded. If, however, an error is detected in the A version of the packet, the A version is discarded and the B version is checked for errors. (In the rare event that an error is also detected in the B version, the B version is discarded, and the R→C packet is lost.) In contrast to prior art spacial diversity techniques in which the decision to switch between antennas is often made after data has already been lost, the present method, through the use of redundant receivers, ensures that the data received from each respective antenna be will available for use.

3. Allocation of Bandwidth to Telemeters

With further reference to FIG. 3, the NET REQ timeslot is used by the telemeters 104 to request timeslot assignments. When the central station receives such a request, it responds (via a control packet) by assigning a timeslot to the requesting telemeter, if a timeslot is available. Thereafter, and until instructed otherwise by the central station 102, the telemeter 104 can use that timeslot to transmit its patient data to the central station.

Advantageously, the system supports the "time sharing" of R→C timeslots by multiple telemeters 104. With time sharing, different telemeters 104 can use the same timeslot in different frames. For example, it is possible to assign four telemeters 104 to timeslot R→$C_0$, in which case the four telemeters will take turns (in an order specified by the central station via the control packet) using the R→$C_0$ timeslot. Time sharing advantageously allows the number of telemeters 104 to be greater than ten, which is the number of R→C timeslots per frame. In the preferred embodiment, each R→C timeslot can be shared by up to 32 different telemeters 104. Thus, up to 10×32=320 telemeters can be used in a single system in the preferred embodiment.

With further reference to FIG. 3, the control packets transmitted during the first two timeslots of a frame each contain a 5-bit frame number and a 1-bit antenna indicator (frame number and antenna indicator not shown). The 5-bit frame number is incremented (from 0 to 31, and then back to zero) by the central station 102 with each successive frame, and serves as a reference to the telemeters 104 for the time sharing of R→C timeslots. The 1-bit antenna indicator simply indicates the antenna (A or B) used to transmit the control packet. The control packets are received by all of the telemeters, and are used to maintain synchronization with the central station 102.

When a control packet is a response to a network request from a telemeter 104, or contains a command to a telemeter, the control packet will contain a telemeter address which uniquely identifies the target telemeter. Two methods of addressing the telemeters are used: When a telemeter 104 is requesting a timeslot, the telemeter is addressed using the telemeter's 24-bit serial number. Once a timeslot has been assigned, the telemeter is addressed by specifying a unique timeslot ID (which ranges 0 to 319) of any timeslot that has been assigned to the telemeter; a timeslot ID of 0 addresses the telemeter that transmits on timeslot R→$C_0$ of frame 0, and a timeslot ID of 319 addresses the telemeter that transmits on timeslot R→$C_9$ of frame 31.

The timeslot allocation options that are supported in the preferred embodiment, and the corresponding baud rate (after overhead) for each such option, are summarized in Table 1. The first row of Table 1 illustrates the case when there is no time sharing. With no time sharing, the telemeter can use the timeslot in every 30 ms frame, and can use the full 9600 baud to transfer its patient data. The bottom row illustrates a time sharing assignment in which the telemeter can use the timeslot in only one out of every 32 frames.

TABLE 1

| NO. TIMES SLOT USED IN 32 FRAMES | MAX BAUD RATE |
| --- | --- |
| 32 | 9600 |
| 16 | 4800 |
| 8 | 2400 |
| 4 | 1200 |
| 2 | 600 |
| 1 | 300 |

In the preferred embodiment, the total available R→C bandwidth of 96,000 baud (9600 baud/timeslot×10 timeslots) is dynamically apportioned among the telemeters 104 based on the respective bandwidth requirements of the telemeters. For example, a relatively small portion (e.g., 300 or 600 baud) of the total R→C bandwidth may be allocated to a telemeter that senses and transmits only numerical data (such as temperature), while a larger portion of the bandwidth (e.g., 4800 or 9600 baud) may be allocated to a telemeter which transmits ECG, voice, or other relatively high bit rate data. Because, as described below, the hardware and firmware of the remote transceivers 112 are configured to maintain the active transmitter components in a low-power state when not in use, this feature of the architecture also serves to conserve battery power.

Although the system described herein is configured to allow a maximum of one timeslot to be assigned to a given telemeter, the software and firmware could be modified to permit multiple timeslots (for example, R→$C_0$ and R→$C_1$) to be allocated to a single telemeter 104. This may be desirable, for example, in applications for which a single telemeter transmits many different types or channels of real time waveform data.

4. Operational Modes

In the preferred embodiment, the system can be selectively operated in any one of three operational modes: (1) a spread spectrum frequency hopping mode which complies with Part 15.247 of the FCC Rules and Regulations, (2) a fixed frequency mode which complies with Part 15.249 of the FCC Rules and Regulations, or (3) a hybrid mode in which the software of the central station 102 selects between the frequency hopping and fixed frequency alternatives. All three of these modes use the TDMA protocol described above.

The mode of operation in which the central station 102 operates may be selected using the mouse and/or keyboard of the host PC 122. The mode in which each telemeter 104 operates may be selected by appropriately positioning a set of DIP switches 410 (FIG. 4) provided on the respective telemeters 104. (While the telemeters could alternatively be configured to switch between the operational modes automatically, the provision of manual switches helps to ensure that the telemeter will not change modes when the patient moves close to a neighboring telemetry system.) As will be appreciated by those skilled in the art, the provision of multiple operational modes provides for the interoperability of the components of the present telemetry system with preexisting systems. Moreover, as will be apparent from the following, the provision of multiple operational modes permits the system to be tailored to the specific requirements (such as the range requirements, and the need, if any, to have multiple systems in close proximity of one another) of the clinic.

The frequency hopping, fixed frequency and hybrid modes are described in-turn below. While these three operational modes all use the 902–928 MHz ISM band, it is contemplated that the system will be configured (through minor changes in firmware, and possibly hardware) to make use of any new frequency bands that may be released by the FCC in the future.

Frequency Hopping Mode

When the telemetry system is operated in the frequency hopping (Part 15.247) mode, the central station 102 and the telemeters synchronously hop (at the beginning of each 30 ms frame) between 53 frequencies within the ISM band. The sequence of 53 frequencies is specified by a pseudo-random function, as required by Part 15.247. In this mode, the central station transmits at the maximum allowable power under Part 15.247 of 1 watt, and the remote transceivers 112 transmit at a default power of 30–50 milliwatts.

When the central station 102 detects that a patient is close to the maximum range at 30–50 milliwatts, as determined using the location code returned by the patient's telemeter 104 and/or the signal strength of the received signal, the central station sends a command to the telemeter to cause the telemeter's remote transceiver 112 to step up its transmit power to 500 milliwatts. (As described below, the remote transceiver's output power can be controlled via the firmware of the transceiver.) Likewise, when the patient subsequently moves sufficiently close to the central station 102, the central station 102 instructs the remote transceiver 112 to reduce its output power to 30–50 milliwatts. In systems that do not include patient locators 150, a similar result can be achieved by configuring the central station software to monitor the bit-error rate in each telemeter's transmissions.

When multiple telemetry systems that operate in the frequency hopping mode are to be placed in close proximity of one another (e.g., within the same hospital), the sequences of 53 frequencies are selected such that an orthogonal relationship exists between the respective sequences. This minimizes the interference between the adjacent systems.

Fixed Frequency Mode

When the telemetry system is operated in the fixed frequency mode, all R→C and C→R transmissions occurs on a single frequency within the ISM band. This frequency is selected upon installation, although the system may optionally be configured to automatically switch to an alternative frequency when high bit-error rates are detected.

The central station 102 and all remote telemeters 104 transmit at 750 μW (microwatts), which is the maximum power permitted under Part 15.249 for single-frequency operation within the ISM band when using a 0.0 dBI gain antenna.

Because the system operates at a lower power in the fixed frequency mode, the range (i.e., the maximum distance between the central station 102 and the telemeters 104) will normally be shorter than for the frequency hopping mode. On the other hand, the fixed frequency mode permits many different systems to be operated in close proximity to one another with little or no interference, since each system can simply be operated on a different fixed frequency. Furthermore, because the telemeters 104 transmit at a lower power, the telemeter battery life will typically be longer in this mode.

Hybrid Mode

In the hybrid mode, the telemetry system normally operates in the fixed frequency mode, but temporarily switches to the frequency hopping mode when either (1) a high bit-error rate is detected or, (2) via a patient locator 150, the central station 102 determines that a patient is near or beyond the maximum range provided by the fixed frequency mode. Telemeter signal strengths may additionally or alternatively be used for this purpose. This mode offers the low power, low interference benefits of the fixed frequency mode, while taking advantage of the greater range which is achievable in the higher-power frequency hopping mode.

5. Remote Transceiver Circuitry

Figures 4, 5:
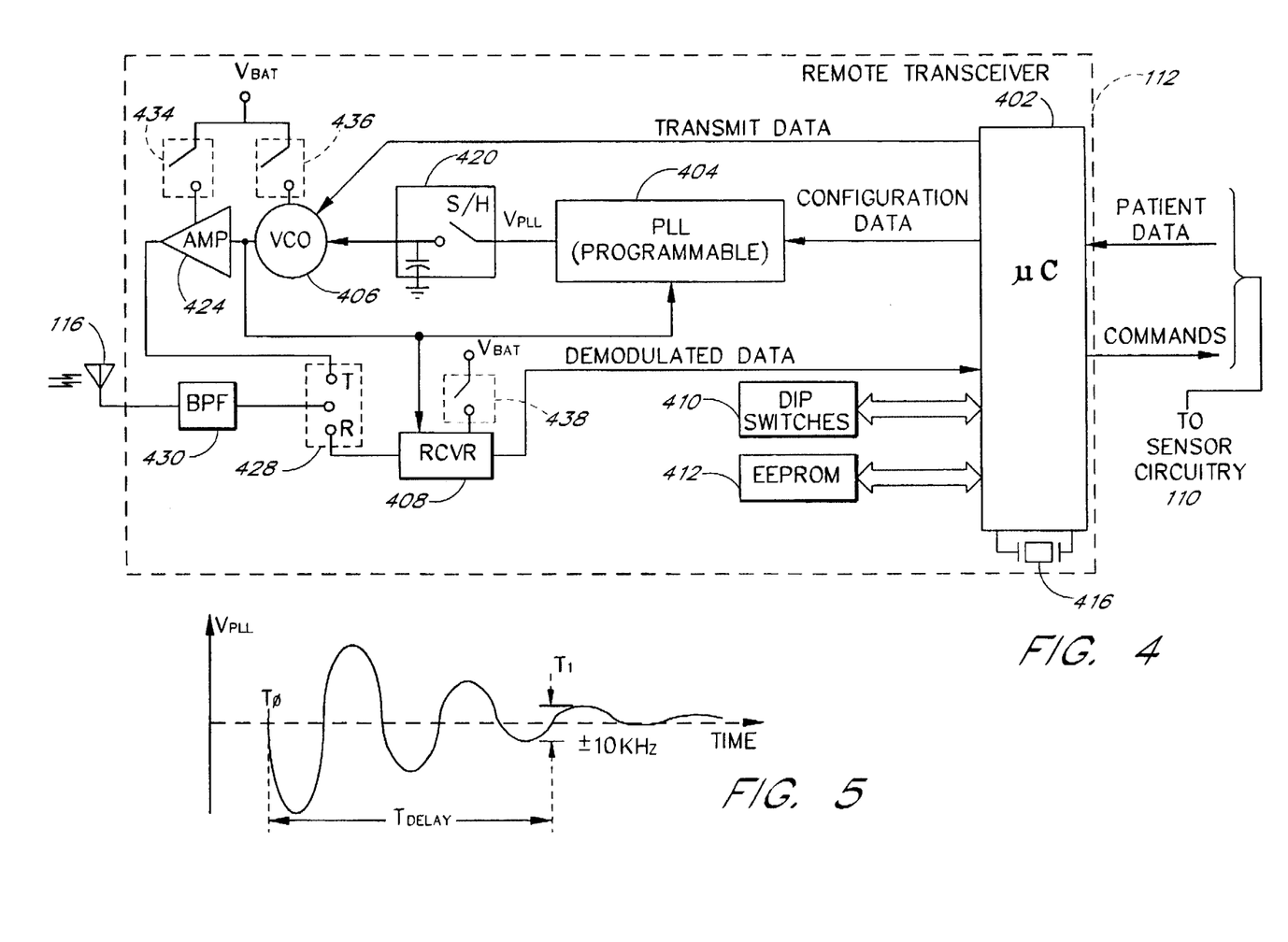
FIG. 4 illustrates the primary components of the remote transceivers of FIG. 1.
FIG. 5 illustrates the output of the phase-locked loop (PLL) of FIG. 4, and is used herein to describe a preferred method for rapidly locking the frequency of the remote transceiver in accordance with the present invention.

FIG. 4 illustrates the primary components of a remote transceiver 112 in accordance with the present invention. The remote transceiver 112 comprises a microcontroller (preferably a 17C42) which is connected, via appropriate port lines, to a programmable phase-locked loop chip 404 (referred to herein as the "PLL 404"), a voltage controlled oscillator (VCO) 406, a receiver (RCVR) 408, a set of DIP (dual in-line package) switches 410, and an EEPROM 412. The PLL 404 is preferably a Motorola MC 145192 which can be placed via appropriate commands into a low-power state when not in use. The microcontroller 402 is clocked by an 8 MHz high stability (±0.001%) crystal oscillator 416.

The output of the PLL 404 is connected as an input to a sample-and-hold (S/H) circuit 420. (The control line from the microcontroller to the sample-and-hold circuit 420 is omitted to simplify the drawing.) The output of the sample-and-hold circuit is connected as the voltage control input to the VCO 406. The output of the VCO is connected to the receiver 408, and is also connected as a feedback input to the programmable PLL 404. The PLL 404 in combination with the VCO 406 form a phase-locked loop.

The output of the amplifier 424 and the signal input of the receiver 408 are connected to respective terminals of a transmit/receive switch 428, which is connected to the antenna 116 via a band-pass filter (BPF) 430. Switches 434, 436, and 438 are provided to selectively apply power ($V_{BAT}$) to the amplifier 424, VCO 406 and receiver 408 respectively. Control lines which connect the microcontroller 402 to the switches 428, 434, 436 and 438 are omitted to simplify the drawing. Also omitted from FIG. 4 is the control line to the amplifier 424 which allows the microcontroller to adjust the output transmission power.

With further reference to FIG. 4, the EEPROM 412 stores various configuration information for the transceiver, in addition to the firmware executed by the microcontroller 402. The configuration information includes, for example, the timeslot assignment (if any), the output power value, the ID of the central station, and the frequencies that are to be skipped during frequency hopping mode operation. The DIP switches 410 are used to select the mode of operation. In other embodiments, the DIP switches are omitted, and the operational modes are selected using software routines. The PLL 404 is programmable via the microcontroller 402, and is used to select the transmit and receive frequencies. As noted above, the PLL is also programmable to a low-power state. The switches 434, 436 and 438 are used to selectively turn on the amplifier 424, VCO 406 and receiver 408 as these components are needed for use.

6. Remote Transceiver Operation

Figure 6:
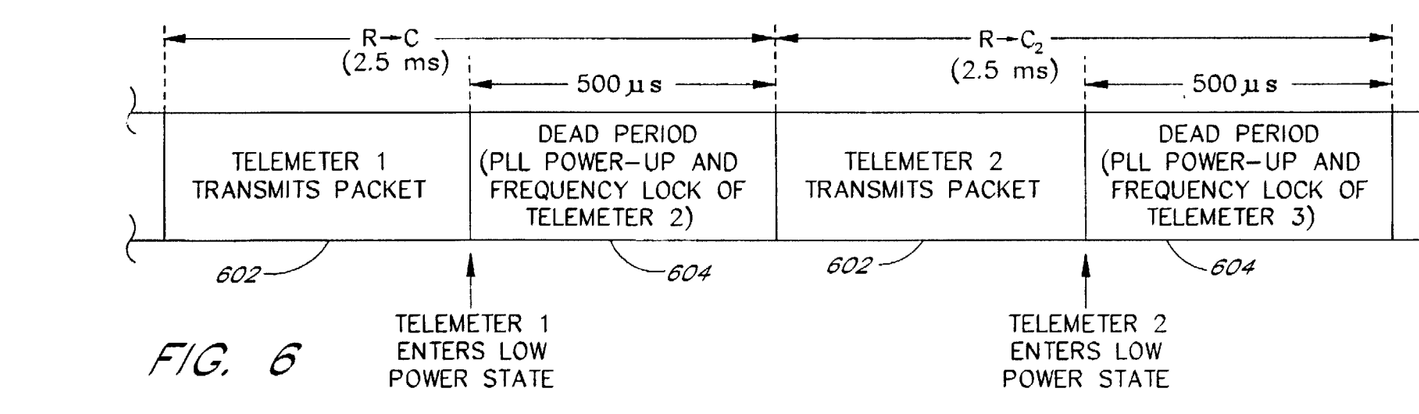
FIG. 6 illustrates a sequence of events that occurs during the R→C TDMA timeslots of FIG. 3.

The general operation of the remote transceiver will now be described with reference to FIGS. 4, 5 and 6. A more detailed description will then be provided with reference to the flow chart of FIGS. 7A and 7B. Referring initially to FIG. 6, each 2.5 ms R→C timeslot comprises a transmit period 602 during which time the assigned remote telemeter 104 transmits its data, followed by a 500 μs dead period 604 during which time no device transmits. The provision of dead periods between successive R→C transmissions ensures that these transmissions will not interfere with one another. As shown in FIG. 6, each remote telemeter 104 is placed in a low-power state (by turning off the VCO 406 and amplifier 424, as described below) once it has finished transmitting its packet.

As indicated in FIG. 6, the dead periods 604 are used in the preferred embodiment to power-up and perform frequency lock of the next remote telemeter 104 to transmit. Because the process of locking the PLL to frequency tends to be a noisy process, which can potentially interfere with the transmissions of other devices, it is desirable to perform frequency lock rapidly, and only when no other device is transmitting its data. Normally, however, the time required to obtain frequency lock using a low-power phase-locked loop is relatively long, approaching or exceeding the 500 μs dead period. Although the dead period could be extended, such an extension would reduce the available bandwidth for data transmissions.

In accordance with one aspect of the invention, a low-power solution to the problem of rapidly achieving frequency lock is provided via the sample-and-hold circuit 420 of FIG. 4, which is used to hold the transient output of the PLL 404 before this output has stopped ringing (or equivalently, before the loop has actually become phase locked). This process is illustrated in FIG. 5, which is an approximate graph of the output ($V_{PLL}$) of the PLL 404 following power-up at $T_0$. Just prior to $T_0$, the VCO 406 is turned on, the sample-and-hold circuit 420 is in the closed (or "sample") position, and the PLL 404 is in the low-power state.

At $T_0$, the PLL 404 is taken out of the low-power state, causing its output $V_{PLL}$ to ring, and thus causing the output of the VCO to oscillate above and below the programmed transmit frequency. Following $T_0$, the output of the PLL is in the general form of a damped sinusoid, which approaches the voltage that corresponds to the programmed frequency. (Because the voltage $V_{PLL}$ controls the VCO 406, the amplitude of the voltage signal in FIG. 5 corresponds to the frequency.) Once this oscillation is sufficiently attenuated such that the frequency error is ±10 KHz ($T_1$ in FIG. 5), the sample-and-hold 420 is opened to thereby hold the input voltage to the VCO 406. This holds the output frequency, and ensures that the remote transceiver's subsequent data transmission will not be contaminated by any oscillation in the PLL's output. Immediately following T1, the amplifier 424 is turned on, the PLL 404 is placed in the low-power state, and the T/R switch 428 is placed in the transmit position. The microcontroller 402 then begins sending its transmit data to the VCO, to thereby FSK-modulate the carrier.

With further reference to FIG. 5, because the transient response of the phase-locked loop (i.e., the PLL 404 in combination with the VCO 406) is highly repeatable, the above result is preferably achieved by simply waiting for a fixed period of time, $T_{DELAY}$, before opening the sample-and-hold 420. In the preferred embodiment, a $T_{DELAY}$ value of 200 μs is used. To ensure that this delay value corresponds to a frequency error within the tolerance of ±10 KHz for each remote transceiver 112, an automated testing procedure is used to select an appropriate value for the programmable gain constant of the remote transceiver's PLL 404. This programmable gain constant value is stored in the telemeter's EEPROM 412, and is loaded into the PLL during use.

Figure 7A:
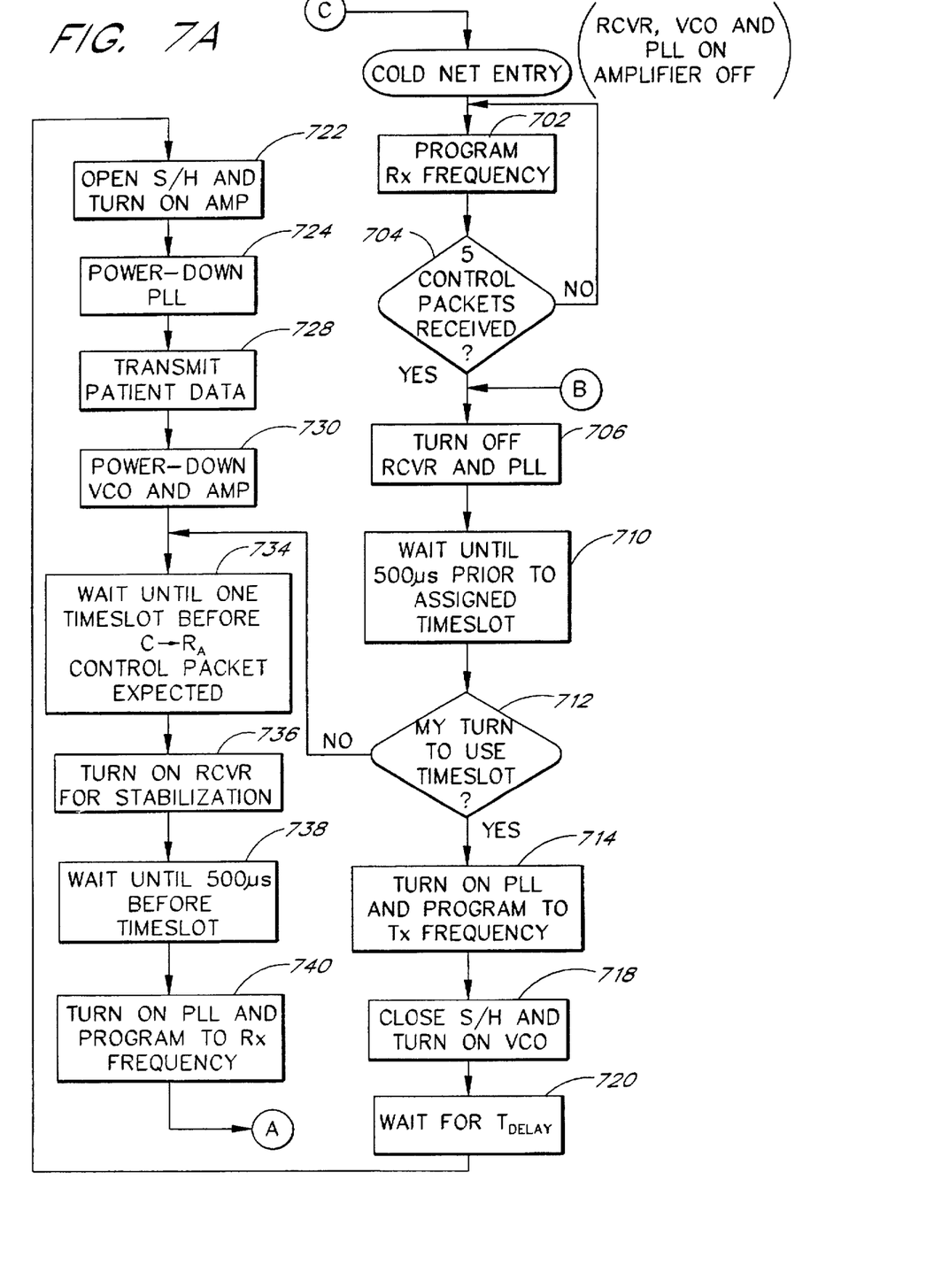
FIGS. 7A and 7B form a flow chart which illustrates a firmware control program executed by the remote transceivers.
Figure 7B:
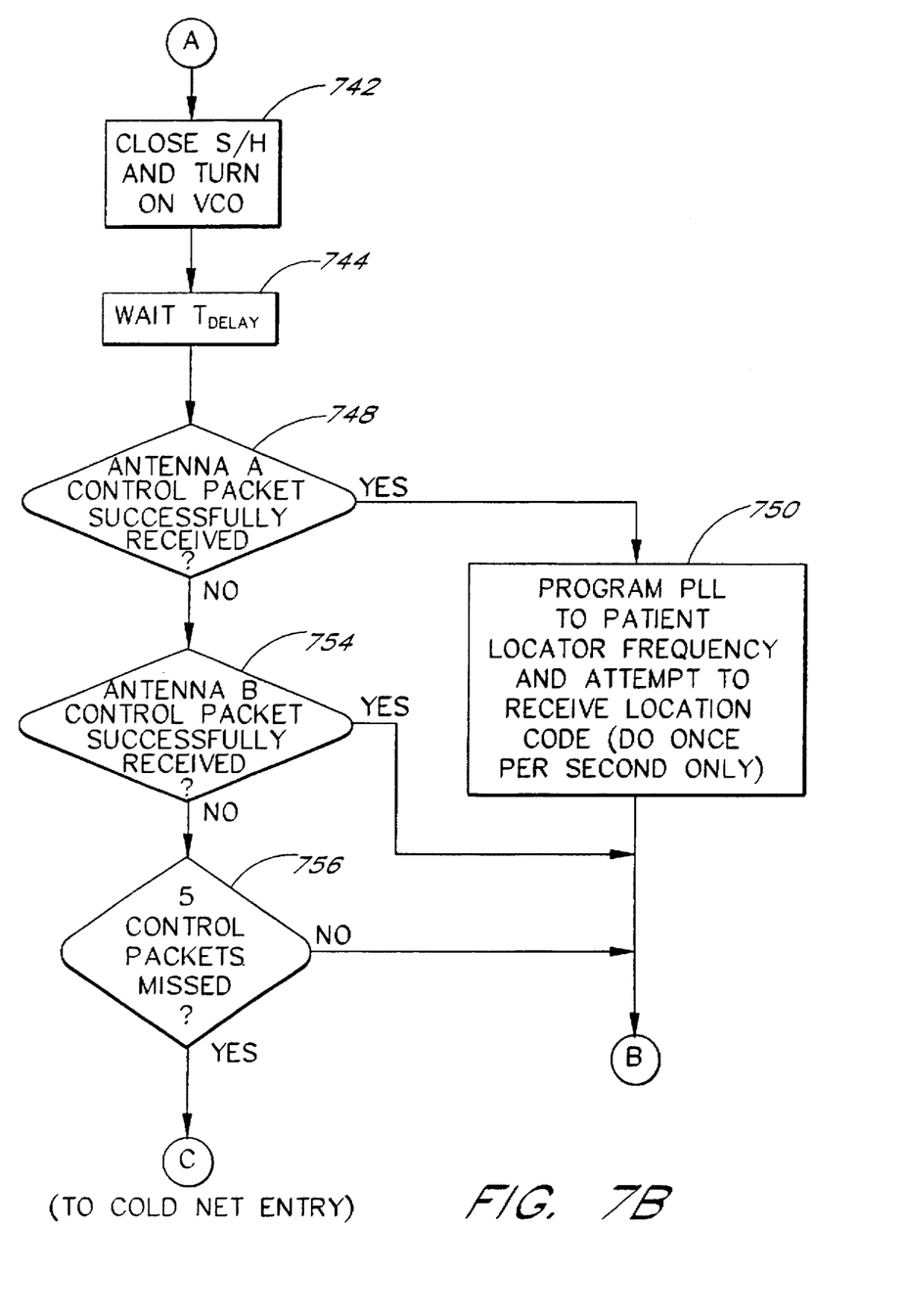

The operation of the system will now be described with reference to FIGS. 7A and 7B, which illustrate a flow chart of the firmware control program executed by the remote transceivers 112. In FIGS. 7A and 7B, the circled characters "A," "B" and "C" represent interconnections between the portions of the flow chart shown in the respective figures. While this flowchart illustrates the primary operations performed during the normal operation of the remote transceiver 112, as will be readily apparent, the flow chart is not intended as a complete specification of every action performed by the microcontroller 402.

With reference to FIG. 7A, when the remote transceiver 112 is initially turned on, it comes up in a receive mode, with the receiver 408, VCO 406 and PLL 404 in the "on" state, and with the amplifier 424 turned off. With reference to blocks 702 and 704, the remote transceiver 112 initially goes through a "cold net entry" sequence in which it attempts to receive and decode control packets transmitted by the central station 102. As part of this sequence, the PLL 404 is programmed to the receive (Rx) frequency. For fixed frequency mode, this is the single frequency of operation. For spread spectrum mode, one of the 53 frequencies in the hopping sequence is selected, and the remote transceiver 112 waits until the central station 102 sweeps across this frequency. (Although not indicated in block 704, when in spread spectrum mode, the receive frequency is hopped as error-free control packets are received.) Once five consecutive control packets have been received with no errors, the remote transceiver 112 is deemed to be in synchronization with the central station 102.

With reference to blocks 706 and 710, the microcontroller 402 then turns off the receiver 408 (to conserve battery power), and then waits until 500 μs prior to the R→C timeslot that has been assigned to the remote telemeter. (This timeslot assignment may be predefined in the EEPROM 412 of the remote transceiver 112, or may be obtained from the central station 102 by generating a network request, depending upon the system's configuration.) With reference to decision block 712, the microcontroller 402 then determines whether or not it is the telemeter's turn to use the timeslot in the current frame. (Unless the timeslot is shared with other telemeters, the result of this determination will always be "yes.") If it is not the telemeter's turn, the microcontroller 402 bypasses the steps of the program that are used to transmit patient data.

With reference to blocks 714 and 718, if it is the telemeter's turn to use the timeslot, the microcontroller 402 turns on the PLL 404 (by taking it out of the low-power state) and loads the PLL with the transmit (Tx) frequency. (In fixed frequency mode, the Tx frequency will always be the same, while in frequency hopping mode, the Tx frequency will be set according to the hopping sequence.) The microcontroller 402 also closes the sample-and-hold 420, and turns on the VCO 406. With reference to block 720, the microcontroller 402 then waits for $T_{DELAY}$ which, as described above, is the period of time needed for the frequency error to settle to within ±10 kHz.

With reference to blocks 722–730, once the frequency error is within ±10 kHz, the microcontroller 402 opens the sample-and-hold 420 (to hold the carrier frequency), turns on the amp, and, to conserve battery power, puts the PLL 404 in its low-power state. The remote transceiver 112 then transmits its packet to the central station 102. Following this transmission, the VCO 406 and amplifier 424 are turned off to conserve battery power.

With reference to blocks 734 and 736, the remote transceiver 112 remains in a low power state until one full timeslot before the C→$R_A$ control packet is expected. At this time, the receiver 408 is turned on, giving the receiver one full R→C timeslot to stabilize before the receipt of the next control packet. With reference to blocks 738–744, 500 µs before the control packet is expected the PLL 404 is turned on and programmed to the receive frequency, and the sample-and-hold 420 is closed and the VCO 406 turned on. Unlike the transmit cycle, the sample-and-hold 420 is preferably kept in the closed position throughout the receive cycle.

With respect to blocks 748 and 750, if the control packet transmitted from antenna A is received successfully (as determined by checking the packet's error detection code), the following timeslot (C→$R_B$) may be used by the remote transceiver to listen for the transmission of a location code from a nearby patient locator 150. Since, as described above, the patient locators 150 transmit their respective codes continuously for one full second at a time (followed by a 15 second pause), the step of checking for the location code is preferably performed only once out of every 33 frames, or approximately once per second.

With respect to blocks 754 and 756, if the control packet transmitted during the C→$R_A$ timeslot is missed, the C→$R_B$ timeslot is used to attempt to receive the redundant transmission (from antenna B) of the control packet. If the antenna B control packet is missed, the microcontroller 402 checks to see if the control packet has been missed on five consecutive frames. If so, the remote transceiver 112 is deemed to have lost synchronization with the central station 102, and the remote transceiver 112 re-enters the synchronization sequence of blocks 702 and 704.

If either (1) the control packet was received during one of the two C→R timeslots, or (2) less than five consecutive control packets have been missed, the program loops back to the point (block 706) at which the receiver 408 and PLL 404 are turned off. The remote transceiver 112 then remains in the low-power "sleep" mode until the next assigned R→C timeslot. Thus, provided that the remote transceiver 112 remains in synchronization with the central station 102, the control program remains in a loop corresponding to blocks 706–756 of the flow chart.

7. Central Transceiver

The hardware arrangement of the central transceiver 126 (shown in high level form in FIG. 1) is similar to that of the remote transceiver 112 of FIG. 4, with several notable exceptions. First, since there is no need to turn off the active components of the central transceiver 126 (since the central transceiver is not powered by battery), the switches 434, 436 and 438 of FIG. 4 are omitted. Second, since the central transceiver 126 needs to be able to simultaneously receive packets from both antennas, it includes two separate receiver circuits (represented by transceivers A and B in FIG. 1). Finally, since power is not a concern, the programmable PLL of FIG. 4 is replaced in the central transceiver 126 with a standard dual DDS (direct digital synthesis) chip (in combination with conventional analog PLLs), with one direct digital synthesizer provided for each receiver.

Figure 8:
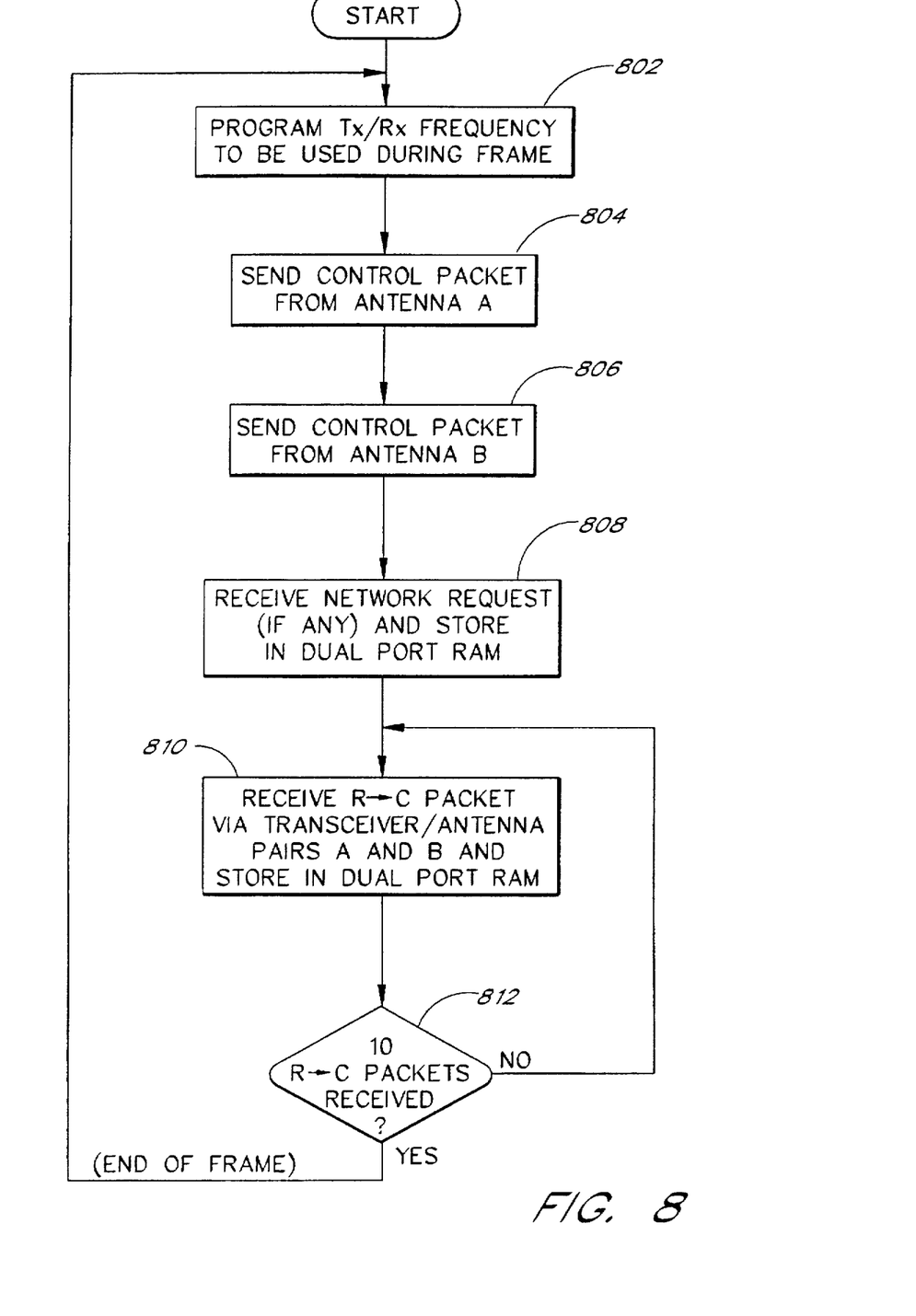
FIG. 8 is a flow chart which illustrates a firmware control program executed by the central transceiver.

FIG. 8 is a flow chart which illustrates the basic operation of the central transceiver 126, as implemented by a firmware control program executed by the central transceiver's microcontroller 130. With reference to block 802, at the beginning of each 30 ms frame the microcontroller 130 programs the transceivers 134 (i.e., the DDS chip) with the single frequency that will be used for all C→R and R→C data transfers during the frame. When the system is operating in the fixed frequency mode, this frequency will always be the same. When operating in the frequency hopping mode, the frequency will be changed with each new frame to the next frequency in the pseudo-random sequence of 53 frequencies.

With reference to blocks 804 and 806, once the frequency has been set, the central transceiver 126 transmits the control packet twice: once from antenna A (during the C→$R_A$ timeslot), and then once from antenna B (during the C→$R_B$ timeslot). As described above, this method of sending data to the remote telemeters 104 advantageously provides spacial diversity (as well as time diversity) without the need for multiple antennas and/or multiple receivers on the remote telemeters 104.

With reference to block 808, after the control packet has been transmitted twice, the central transceiver 126 attempts to receive any network requests that may be transmitted during the NET REQ timeslot (FIG. 3). If a network request is received, it is written to the dual-port RAM 138 for subsequent processing by the communications routines running on the host PC 122. The use of a contention timeslot for transferring network requests, as opposed to a strict TDMA scheme in which each telemeter has its own dedicated network request timeslot, provides for a high degree of bandwidth efficiency, since the telemeters 104 generate network requests on a relatively infrequent basis. As with the R→C (patient data) packets, the network request packets are received using both antennas 125.

With reference to blocks 810 and 812, the central transceiver 126 then enters into a loop in which it receives, in order, the ten packets corresponding to timeslots R→$C_0$ to R→$C_9$. As described above, each R→C packet is received twice (simultaneously), once from each antenna, and the antenna A and antenna B versions of the each packet are written to the dual-port RAM 138 for subsequent error checking and processing by the host PC's software. Once all ten R→C packets have been received (regardless of whether any errors were present in the packets), the control program loops back and begins a new frame.

While the present invention has been described herein with reference to a preferred medical telemetry system, it will be recognized that the present invention is not so limited. For example, it will be recognized that the low-power circuitry and method disclosed herein for raplidly locking a carrier frequency can be utilized in other types of wireless devices, including two-way pagers, cellular telephones, non-medical telemetry devices, wireless personal digital assistants, PCS devices, and other types of messaging devices. It will also be regonized that the invention is not limited to devices which communicate using a TDMA protocol, and may be used, for example, by devices which automatically switch between a plurality of transmit frequencies. Accordingly, the scope of the present invention should be defined only in accordance with the following claims.

In the claims which follow, alphabetic characters used to designate claim steps are provided for convenience of description only, and are not intended to imply any particular order for performing the corresponding steps.

What is claimed is:

1. A method of rapidly locking the carrier frequency of a wireless communications device, comprising the steps of:

(a) providing a phase-lock loop (PLL) circuit having a sample-and-hold circuit connected to an input of a voltage-controlled oscillator (VCO), an output of said VCO providing a carrier signal for transmitting and/or receiving data;

(b) closing a loop of said PLL circuit to initiate a phase-lock process;

(c) waiting a predetermined delay after said closing to allow a frequency of said carrier signal to settle to within a selected acceptable margin of error from a predetermined carrier frequency, said predetermined delay being shorter than a delay required for said PLL circuit to reach a phase-locked state; and (d) opening said sample-and-hold circuit at the end of said predetermined delay to thereby hold said carrier signal at a constant frequency which falls within said selected acceptable margin of error.

2. The method according to claim 1, wherein said communications device transmits data during an assigned slot of a time-division multiple access (TDMA) frame, and wherein steps (b), (c) and (d) are performed periodically during each assigned slot.

3. The method according to claim 1, further comprising the step of:

(e) using said carrier signal at said constant frequency to transmit data from said communications device.

4. The circuit according to claim 3, wherein said selected margin of error is selected such that a receiver accurately receives said data transmitted in step (e) as though transmitted using said predetermined carrier frequency.

5. The method according to claim 1, wherein said predetermined carrier frequency falls within the ISM band.

6. The method according to claim 5, wherein said acceptable margin of error is greater than ±5 KHz.

7. The method according to claim 1, wherein said PLL circuit comprises a programmable PLL chip which has a low-power state and an operational state, and wherein said step of closing said loop comprises switching said PLL chip from said low-power state to said operational state.

8. The method according to claim 7, further comprising a calibration step of adjusting a programmable gain constant of said PLL chip such that said predetermined delay corresponds to said selected acceptable margin of error.

9. The method according to claim 7, further comprising the steps of:

after opening said sample-and-hold circuit, placing said PLL chip in said low-power state to conserve power; and while said PLL chip is in said low-power state, transmitting or receiving data with said communications device.

10. A method of locking a carrier frequency of a battery-powered communications device, said communications device comprising a phase-lock loop (PLL) circuit for generating a carrier signal in a period of time less than required to reach a phase-locked state, the method comprising the steps of:

closing a loop of said PLL circuit to thereby initiate a phase-lock process;

interrupting said phase-lock process after said carrier signal has settled to within a selected acceptable margin of frequency error but before said PLL circuit reaches a phase-locked state, said step of interrupting comprising freezing said carrier signal at a fixed frequency; and transmitting a data packet from said communications device using said carrier signal at said fixed frequency.

11. The method according to claim 10, wherein said fixed frequency falls within the ISM band, and wherein said acceptable margin of frequency error is greater than ±5 KHz.

12. The method according to claim 10, wherein said step of interrupting comprises opening said loop.

13. The method according to claim 10, wherein said PLL circuit comprises a voltage-controlled oscillator, and wherein said step of interrupting comprises freezing a control input of said voltage-controlled oscillator at a fixed voltage.

14. The method according to claim 13, wherein said step of freezing said control input comprises placing a sample-and-hold circuit in a HOLD state.

15. The method according to claim 10, wherein said step of closing said loop is performed periodically at the beginning of a time-division multiple access (TDMA) time slot assigned to said communications device.

16. The method according to claim 15, wherein said PLL circuit comprises a programmable PLL chip which is switchable between a low-power state and an operational state, and wherein said step of closing said loop comprises switching said PLL chip from said low-power state to said operational state.

17. The method according to claim 16, further comprising switching said PLL chip to said low-power state immediately after said step of interrupting, to thereby conserve power during said transmitting of said data packet.

18. A low-power circuit for rapidly locking the frequency of a carrier signal, comprising:

a programmable phase-lock loop (PLL) chip coupled to a voltage-controlled oscillator (VCO) to form a PLL circuit, an output of said VCO circuit providing said carrier signal; and a sample-and-hold circuit connected between said PLL chip and said VCO such that a feedback loop of said PLL circuit is closed when said sample-and-hold circuit is in a SAMPLE state, and such that said feedback loop is open when said sample-and-hold circuit is in a HOLD state, said sample-and-hold circuit thereby allowing said carrier signal to be held at a fixed frequency without waiting for said PLL circuit to reach a phase-locked state.

19. The circuit according to claim 18, wherein said programmable PLL chip is switchable between a low-power state and an operational state.

20. The circuit according to claim 18, further comprising a microcontroller coupled to said programmable PLL chip and said sample-and-hold circuit, said microcontroller programmed to perform a rapid frequency lock operation by performing the steps of:

(a) closing said feedback loop to initiate a phase-lock process;

(b) waiting a predetermined delay after closing said feedback loop to allow said carrier signal to settle to within a selected frequency margin of a predetermined carrier frequency; and (c) immediately following step (b), placing said sample-and-hold circuit in said HOLD state to lock the frequency of said carrier signal.

21. The circuit according to claim 20, wherein said programmable PLL chip has a programmable gain constant, said programmable gain constant programmed such that said predetermined delay corresponds to said acceptable margin of frequency error.

22. The circuit according to claim 20, further comprising a data transmission circuit coupled to said output of said VCO, and wherein said microcontroller is programmed to periodically transmit data packets during a time slot of a TDMA frame.

23. The method according to claim 20, wherein said acceptable margin of frequency error is at least ±7 KHz.

24. A battery-powered remote telemeter, comprising:
- a transceiver circuit comprising a phase-lock loop (PLL) circuit, said PLL circuit having a sample-and-hold circuit connected in a feedback loop thereof, said sample-and-hold circuit connected such that said feedback loop is closed when said sample-and-hold circuit is in a SAMPLE state, and such that said feedback loop is open when said sample-and-hold circuit is in a HOLD state; and
- a battery-powered microcontroller coupled to said transceiver circuit, said microcontroller programmed to send and receive data packets via said transceiver circuit using a two-way TDMA data transfer protocol.

25. The battery-powered remote telemeter according to claim 24, wherein said PLL circuit comprises a programmable PLL chip, said programmable PLL chip switchable between a low-power state and an operational state.

26. The battery-powered remote telemeter according to claim 24, wherein said microcontroller is programmed to periodically lock a carrier frequency of said transceiver circuit by:
- (a) closing said feedback loop to initiate a phase-lock process;
- (b) waiting for a predetermined delay after closing said feedback loop to allow a carrier signal generated by said PLL circuit to settle to within a selected acceptable margin of frequency from a predetermined carrier frequency; and
- (c) immediately following step (b), placing said sample-and-hold circuit in said HOLD state to prevent said carrier signal from oscillating in frequency during a transmission of data.

27. The battery-powered remote telemeter according to claim 26, wherein said acceptable margin of frequency is selected such that a resulting carrier frequency is sufficiently close to said predetermined carrier frequency that a receiver accurately receives the transmission of data as if transmitted using said predetermined carrier frequency.

* * * * *